(12) United States Patent
Takimoto et al.

(10) Patent No.: US 8,125,311 B2
(45) Date of Patent: Feb. 28, 2012

(54) MEDICAL DIAGNOSTIC IMAGING SYSTEM, INFORMATION PROCESSING METHOD FOR MEDICAL DIAGNOSTIC IMAGING SYSTEM, ULTRASONIC IMAGING DIAGNOSTIC APPARATUS, AND OPERATION DEVICE

(75) Inventors: Masao Takimoto, Otawara (JP); Muneki Kataguchi, Nasushiobara (JP); Fumiyasu Sakaguchi, Otawara (JP); Akihiro Kakee, Nasushiobara (JP); Tomohisa Imamura, Nasushiobara (JP); Shigemitsu Nakaya, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1107 days.

(21) Appl. No.: 11/877,283

(22) Filed: Oct. 23, 2007

(65) Prior Publication Data
US 2008/0097205 A1    Apr. 24, 2008

(30) Foreign Application Priority Data
Oct. 24, 2006   (JP) .............................. P2006-289143

(51) Int. Cl.
| | |
|---|---|
| A61B 8/00 | (2006.01) |
| H04W 24/00 | (2009.01) |
| G05B 19/00 | (2006.01) |
| G05B 23/00 | (2006.01) |
| G06F 7/00 | (2006.01) |
| G06F 7/04 | (2006.01) |
| G06K 19/00 | (2006.01) |
| G08B 29/00 | (2006.01) |
| G08C 19/00 | (2006.01) |
| H04B 1/00 | (2006.01) |
| H04B 3/00 | (2006.01) |
| H04L 9/14 | (2006.01) |
| H04L 9/32 | (2006.01) |
| H04Q 1/00 | (2006.01) |
| H04Q 9/00 | (2006.01) |

(52) U.S. Cl. .......................... 340/5.2; 455/425; 600/437
(58) Field of Classification Search ................... 600/437
See application file for complete search history.

(56) References Cited

U.S. PATENT DOCUMENTS
| | | | |
|---|---|---|---|
| 6,773,398 B2 * | 8/2004 | Ogasawara et al. | 600/437 |
| 2003/0088290 A1 * | 5/2003 | Spinelli et al. | 607/30 |
| 2005/0049495 A1 * | 3/2005 | Sumanaweera et al. | 600/437 |
| 2007/0204231 A1 * | 8/2007 | Cunningham et al. | 715/734 |
| 2010/0323690 A1 * | 12/2010 | Shaw | 455/425 |

FOREIGN PATENT DOCUMENTS
| | | |
|---|---|---|
| JP | 2001-137237 | 5/2001 |
| JP | 2003-153903 | 5/2003 |

* cited by examiner

Primary Examiner — Benjamin C Lee
Assistant Examiner — Cal Eustaquio
(74) Attorney, Agent, or Firm — Oblon, Spivak, McClelland, Maier & Neustadt, L.L.P.

(57) ABSTRACT

Provided is a medical diagnostic imaging system in which user information can be easily and efficiently moved (transferred) among a plurality of ultrasonic imaging diagnostic apparatuses. The medical diagnostic imaging system includes: a plurality of ultrasonic imaging diagnostic apparatuses each including a recording unit for recording user information registered by a user, the user information including work flow data for guiding at least an operation procedure of the ultrasonic imaging diagnostic apparatus, and execution means for executing this user information; and user information transfer means configured to be able to communicate with the ultrasonic imaging diagnostic apparatuses, for transferring the user information recorded on the recording means of a predetermined one of the ultrasonic imaging diagnostic apparatuses to the recording means of a different one of the ultrasonic imaging diagnostic apparatuses by way of a communication.

16 Claims, 7 Drawing Sheets

WELCOME
You are Mr. X.
Presonal Information is as below.

Category1
☑ Information A
☐ Information B
☐ Information C
☐ Information D
☑ Information E
☐ Information F Category2
☐ Protocol A
☐ Protocol B
☐ Protocol C
☑ Protocol D
☐ Protocol E
☐ Protocol F Category3
☐ Preset A
☐ Preset B
☑ Preset C
☐ Preset D
☐ Preset E
☐ Preset F

[Send] [Cancel]

MEDICAL DIAGNOSTIC IMAGING SYSTEM, INFORMATION PROCESSING METHOD FOR MEDICAL DIAGNOSTIC IMAGING SYSTEM, ULTRASONIC IMAGING DIAGNOSTIC APPARATUS, AND OPERATION DEVICE

BACKGROUND OF THE INVENTION

1. Field of the Invention

The present invention relates to a medical diagnostic imaging system provided with a plurality of ultrasonic imaging diagnostic apparatuses, an operation device for remotely operating the diagnostic apparatuses, and the like, an information processing method for the medical diagnostic imaging system, an ultrasonic imaging diagnostic apparatus, and an operation device. In particular, the invention relates to a medical diagnostic imaging system provided with an operation device configured to be able to transfer user information including work flow data which is incorporated in a predetermined ultrasonic imaging diagnostic apparatus to another ultrasonic imaging diagnostic apparatus, an information processing method for the medical diagnostic imaging system, an ultrasonic imaging diagnostic apparatus, and an operation device.

2. Description of the Related Art

For ultrasonic imaging diagnostic apparatuses of recent years, various examination methods have been proposed such as Tissue Doppler Imaging (TDI) for visualizing the movement of a tissue of a subject and 3D Tissue Imaging for three-dimensionally displaying the tissue of the subject.

However, in order to execute these examination methods, an extremely large number of switch operations (by using a key board, a touch panel, a track ball, a mouse, etc.) are required. An operator (user) such as a doctor or a technician conducts a diagnosis by making full use of the above-mentioned examination methods, clinical applications, and measurement functions thereof. Therefore, it is necessary for the user such as the doctor or the technician to learn an operation method of the ultrasonic imaging diagnostic apparatus for the above-mentioned individual examination methods and the like.

For this reason, the operation method of the ultrasonic imaging diagnostic apparatus becomes complicated and diversified. In a case where the diagnostic apparatus is actually operated, a particularly high level of techniques and experiences is required. For this reason, variations in operation techniques and experience are common, and there is a possibility of degrading the reliability of examination results.

In addition, along with the spread of the ultrasonic diagnostic apparatuses, the number of inexperienced technicians tends to be increased. For this reason, there is a demand of an ultrasonic imaging diagnostic apparatus whose operation method can be quickly learnt and which can be easily operated.

In view of the above, an ultrasonic imaging diagnostic apparatus provided with a work flow system for guiding an operation method of the ultrasonic imaging diagnostic apparatus has been recently proposed (for example, refer to Japanese Unexamined Patent Application Publication No. 2001-137237).

Also, an ultrasonic imaging diagnostic apparatus provided with an operation device for remotely operating the ultrasonic imaging diagnostic apparatus on user's hands has been proposed (for example, refer to Japanese Unexamined Patent Application Publication No. 2003-153903).

Execution procedures of the above-mentioned work flow system are varied depending on the users such as the doctors and the examination technicians, and such a configuration is adopted that the work flow system can be executed by work flow data which is customized conforming to the skill and technique of the respective users. For this reason, the examination efficiency is satisfactory and the lack of an examination can also be prevented.

While using the individually customized work flow, the users also customize and use user registration data (examiner registration data) in parallel such as a key arrangement of an operation panel of the ultrasonic imaging diagnostic apparatus, a position and a height of the operation panel, a monitor luminance, an image quality condition, a setting of body marks, settings and the like of various measurement methods, and default setting values thereof.

The registration data is also user information similar to the work flow, and it is necessary to safely manage the registration data as well as diagnosis data of a patient (subject) who has been screened (diagnosed) by the user (examiner).

However, in such a conventional ultrasonic imaging diagnostic apparatus, the user information such as the work flow data is customized for each ultrasonic imaging diagnostic apparatus. In a use site such as a hospital provided with a plurality of the above-mentioned ultrasonic imaging diagnostic apparatuses, even though the user individually customizes the user information such as the work flow data, if the user cannot use the usually used accustomed ultrasonic imaging diagnostic apparatus due to any cause, the user needs to use a different ultrasonic imaging diagnostic apparatus which is customized by another user. Therefore, there is a problem of decreasing the throughput of the examination service.

Also, in this case, it is also conceivable to use a method of temporarily moving the customized user information such as the work flow data from the ultrasonic imaging diagnostic apparatus to a removable medium such as an MO or a CD and further moving the customized user information from this removable medium to the different ultrasonic imaging diagnostic apparatus which will be used, but the efficiency is extremely low.

SUMMARY OF THE INVENTION

Accordingly, the present invention has been made in view of the above-mentioned circumstances, and it is an object of the invention to provide a medical diagnostic imaging system in which user information can be easily and efficiently moved (transferred) among a plurality of ultrasonic imaging diagnostic apparatuses, an information processing method for the medical diagnostic imaging system, an ultrasonic imaging diagnostic apparatus, and an operation device.

In order to attain the above-mentioned object, according to a first aspect of the present invention, there is provided a medical diagnostic imaging system, including: an ultrasonic imaging diagnostic apparatus and an operation device connected to the ultrasonic imaging diagnostic apparatus so as to be able to perform a data communication, wherein: the operation device comprises: a first memory unit configured to memorize authentication information used for authenticating a user operating the operation device; an access restriction unit configured to authenticate whether or not the user operating the operation device is permitted to access the ultrasonic imaging diagnostic apparatus on the basis of the authentication information memorized in the first unit, and if the user operating the operation device is permitted to access the ultrasonic imaging diagnostic apparatus, permitting an access to the ultrasonic imaging diagnostic apparatus, and if the user operating the operation device is not permitted to access the ultrasonic imaging diagnostic apparatus, restricting the access to the ultrasonic imaging diagnostic apparatus; and a control unit configured to control operation of the ultrasonic imaging diagnostic apparatus, if the access to the ultrasonic imaging diagnostic apparatus is permitted by the access restriction unit, controlling so as to permit the operation of the ultrasonic imaging diagnostic apparatus, if the access to the ultrasonic imaging diagnostic apparatus is restricted by the access restriction unit, controlling so as to partly restrict the operation of the ultrasonic imaging diagnostic apparatus.

In order to attain the above-mentioned object, according to a second aspect of the present invention, there is provided an information processing method for a medical diagnostic imaging system, including: an ultrasonic imaging diagnostic apparatus and an operation device connected to the ultrasonic imaging diagnostic apparatus so as to be able to perform a data communication, wherein: the operation device performs: memorizing authentication information used for authenticating a user operating the operation device; authenticating whether or not the user operating the operation device is permitted to access the ultrasonic imaging diagnostic apparatus on the basis of the authentication information memorized in the operation device, and if the user operating the operation device is permitted to access the ultrasonic imaging diagnostic apparatus, permitting an access to the ultrasonic imaging diagnostic apparatus, and if the user operating the operation device is not permitted to access the ultrasonic imaging diagnostic apparatus, restricting the access to the ultrasonic imaging diagnostic apparatus; and controlling operation of the ultrasonic imaging diagnostic apparatus, if the access to the ultrasonic imaging diagnostic apparatus is permitted by the access restriction unit, controlling so as to permit the operation of the ultrasonic imaging diagnostic apparatus, if the access to the ultrasonic imaging diagnostic apparatus is restricted by the access restriction unit, controlling so as to partly restrict the operation of the ultrasonic imaging diagnostic apparatus.

In order to attain the above-mentioned object, according to a third aspect of the present invention, there is provided a medical diagnostic imaging system, including: an ultrasonic imaging diagnostic apparatus and an operation device connected to the ultrasonic imaging diagnostic apparatus so as to be able to perform a data communication, wherein: the ultrasonic imaging diagnostic apparatus comprises: a recording unit configured to record user information registered by the user, including work flow data for guiding at least an operation procedure of the ultrasonic imaging diagnostic apparatus; an execution unit configured to execute the user information recorded by the recording unit; and a control unit configured to control operation of the ultrasonic imaging diagnostic apparatus; the operation device comprises: a first memory unit configured to memorize authentication information used for authenticating the user operating the operation device; and an access restriction unit configured to authenticate whether or not the user operating the operation device is permitted to access the ultrasonic imaging diagnostic apparatus on the basis of the authentication information memorized in the first unit, and if the user operating the operation device is permitted to access the ultrasonic imaging diagnostic apparatus, permitting an access to the ultrasonic imaging diagnostic apparatus, and if the user operating the operation device is not permitted to access the ultrasonic imaging diagnostic apparatus, restricting the access to the ultrasonic imaging diagnostic apparatus; wherein the control unit configured to control operation of the ultrasonic imaging diagnostic apparatus, if the access to the ultrasonic imaging diagnostic apparatus is permitted by the access restriction unit, controlling so as to permit the operation of the ultrasonic imaging diagnostic apparatus, if the access to the ultrasonic imaging diagnostic apparatus is restricted by the access restriction unit, controlling so as to partly restrict the operation of the ultrasonic imaging diagnostic apparatus.

In order to attain the above-mentioned object, according to a forth aspect of the present invention, there is provided an ultrasonic imaging diagnostic apparatus, including: a recording unit configured to record user information registered by the user, including work flow data for guiding at least an operation procedure of an ultrasonic imaging diagnostic apparatus connected to an operation device so as to be able to perform a data communication; an execution unit configured to execute the user information recorded by the recording unit; and a control unit configured to control operation of the ultrasonic imaging diagnostic apparatus; wherein the control unit configured to control operation of the ultrasonic imaging diagnostic apparatus, if the access to the ultrasonic imaging diagnostic apparatus is permitted by the access restriction unit, controlling so as to permit the operation of the ultrasonic imaging diagnostic apparatus, if the access to the ultrasonic imaging diagnostic apparatus is restricted by the access restriction unit, controlling so as to partly restrict the operation of the ultrasonic imaging diagnostic apparatus.

In order to attain the above-mentioned object, according to a fifth aspect of the present invention, there is provided an operation device, including: a first memory unit configured to memorize authentication information used for authenticating a user operating the operation device connected to the ultrasonic imaging diagnostic apparatus so as to be able to perform a data communication; an access restriction unit configured to authenticate whether or not the user operating the operation device is permitted to access the ultrasonic imaging diagnostic apparatus on the basis of the authentication information memorized in the first unit, and if the user operating the operation device is permitted to access the ultrasonic imaging diagnostic apparatus, permitting an access to the ultrasonic imaging diagnostic apparatus, and if the user operating the operation device is not permitted to access the ultrasonic imaging diagnostic apparatus, restricting the access to the ultrasonic imaging diagnostic apparatus; and a control unit configured to control operation of the ultrasonic imaging diagnostic apparatus, if the access to the ultrasonic imaging diagnostic apparatus is permitted by the access restriction unit, controlling so as to permit the operation of the ultrasonic imaging diagnostic apparatus, if the access to the ultrasonic imaging diagnostic apparatus is restricted by the access restriction unit, controlling so as to partly restrict the operation in the ultrasonic imaging diagnostic apparatus.

DESCRIPTION OF THE PREFERRED EMBODIMENTS

Hereinafter, embodiments of the present invention will be described with reference to the accompanying drawings. It should be noted that the same reference numerals are allocated to the same or equivalent parts in the plurality of accompanying drawings.

Figure 1:
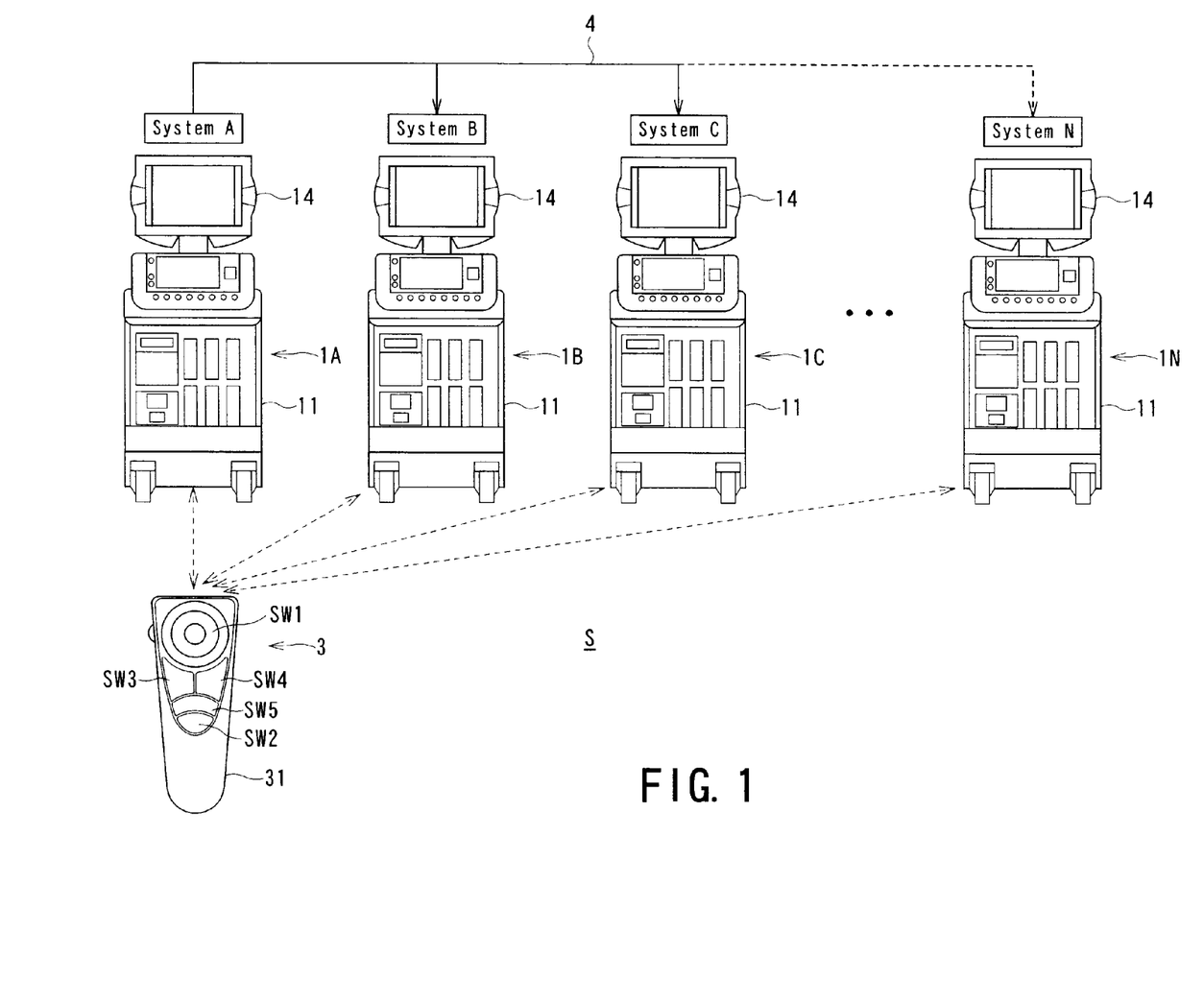
FIG. 1 is a schematic diagram illustrating an entire configuration of a medical diagnostic imaging system according to a first embodiment of the present invention.
Figure 2:
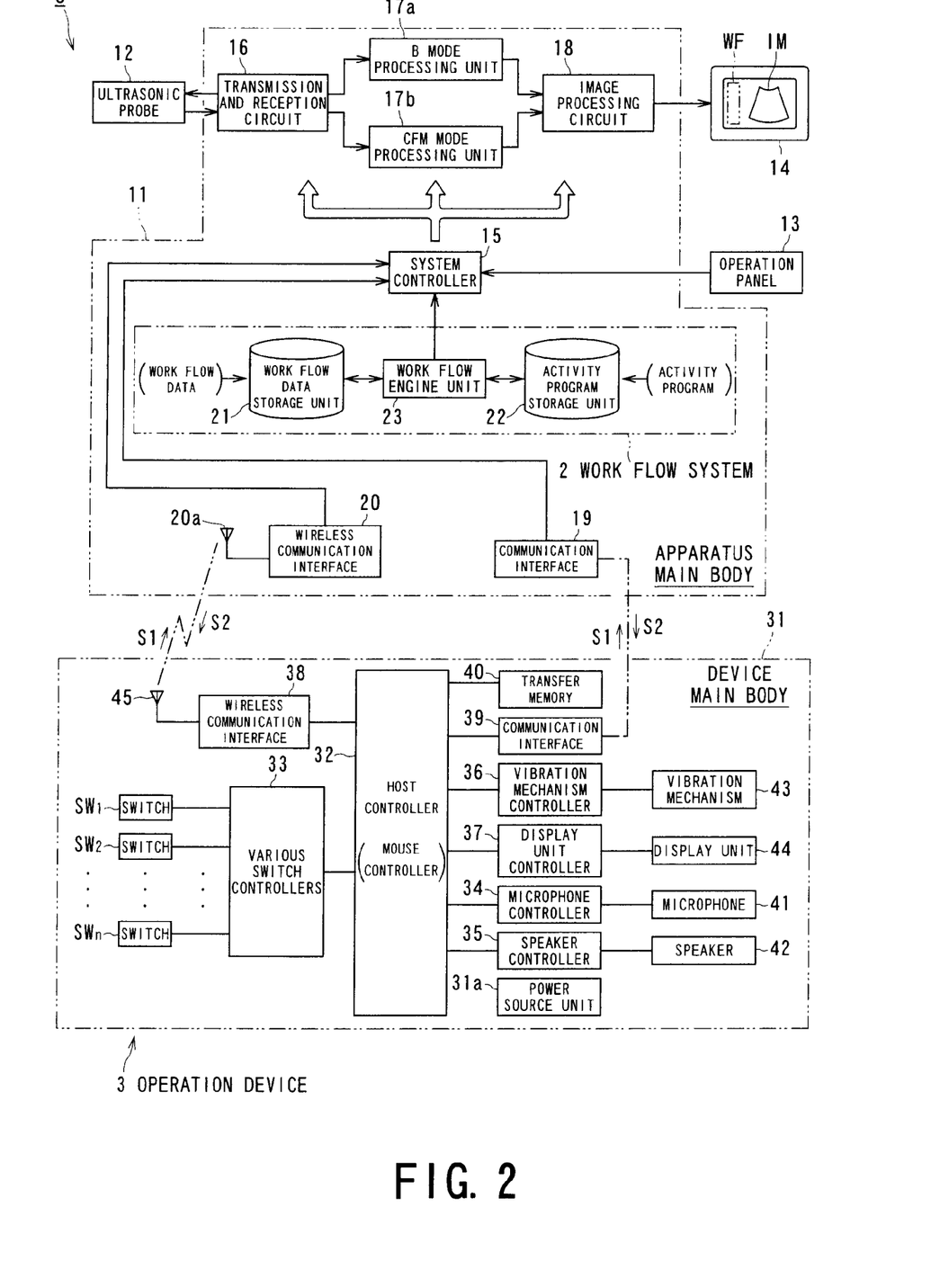
FIG. 2 is a function block diagram illustrating configurations of an ultrasonic imaging diagnostic apparatus and an operation device illustrated in FIG. 1.

FIG. 1 is a schematic diagram illustrating an entire configuration of a medical diagnostic imaging system S according to a first embodiment of the present invention. FIG. 2 is a function block diagram illustrating respective functions of an ultrasonic imaging diagnostic apparatus 1 and an operation device 3 which constitute the medical diagnostic imaging system S.

As illustrated in FIG. 1, the medical diagnostic imaging system S is referred to as work flow system (which is also referred to as "Protocol Assistant System: PAS" and hereinafter, which is abbreviated as "WFS" for convenience in the description of this embodiment). The medical diagnostic imaging system S is provided with a plurality of ultrasonic imaging diagnostic apparatuses 1A to 1N each having the WFS as one type of user information, and at least one operation device 3 which includes remote operation means for remotely operating the ultrasonic imaging diagnostic apparatuses 1A to 1N and information movement (transfer) means for moving the user information including work flow data recorded on recording means, which will be described later, of the ultrasonic imaging diagnostic apparatuses 1A to 1N via a LAN 4.

As illustrated in FIG. 2, each of the ultrasonic imaging diagnostic apparatuses 1A to 1N includes, as a hardware configuration, an apparatus main body 11, an ultrasonic probe 12 connected to the apparatus main body 11, an operation panel 13, and a monitor 14. Input devices such as switches, buttons, a key board, a track ball, and a mouse are mounted to the operation panel 13.

The ultrasonic probe 12 is a device (probe) for transmitting and receiving an ultrasonic signal irradiated to or reflected from a subject, and is composed of piezoelectric elements such as piezoelectric ceramics functioning as electro/mechanical reversible conversion elements. The probe 12 is structured of a phased array type in which a plurality of piezoelectric elements arranged in an array are arranged at a distal end part, for example. With this configuration, the probe 12 converts a pulse drive voltage supplied from a transmission and reception circuit 16 of the apparatus main body 11 into an ultrasonic pulse signal to transmit the signal in a desired direction within a scan area of the subject (patient) which is not illustrated in the drawing, and also receives an ultrasonic echo signal reflected from the subject to convert the signal into an echo signal having a voltage corresponding to ultrasonic echo signal.

The apparatus main body 11 includes, as well as a system controller 15 functioning as a control center of the entire ultrasonic imaging diagnostic apparatus 1, various units operating under the control of the system controller 15, that is, the transmission and reception circuit 16, a B mode processing unit 17a, a CFM (color flow mapping) mode processing unit 17b, and an image processing circuit 18. In addition, a communication interface (based on a predetermined communication standard such as USB or IEEE1394) 19 which can communicate with the operation device 3, and a wireless communication interface (infrared communication (IrDA), electric waves (based on a predetermined wireless communication standard such as Bluetooth or IEEE802.11) etc.) 20 are mounted to the apparatus main body 11. An antenna unit 20a including an infrared communication window, a wireless antenna, and the like is connected to the wireless communication interface 20.

The transmission and reception circuit 16 transmits a drive signal to each piezoelectric element of the ultrasonic probe 12 at a timing to which a predetermined transmission delay time is added for each transmission channel based on a control signal from the system controller 15, whereby the ultrasonic signal is transmitted from each piezoelectric element of the ultrasonic probe 12 into a body of the subject. On the other hand, the transmission and reception circuit 16 receives the ultrasonic echo signal including components reflected by boundaries different in acoustic impedance in the body of the subject and diffused by a scattering body in a tissue in accordance with the transmission of the ultrasonic signal via each piezoelectric element of the ultrasonic probe 12 as an echo signal having a voltage corresponding thereto. Then, the transmission and reception circuit 16 performs a reception delay and addition processing on the echo signal and outputs the processed reception signal to the B mode processing unit 17a and the CFM mode processing unit 17b in the next stage, respectively.

The B mode processing unit 17a performs an envelope detection on the reception signal from the transmission and reception circuit 16 and outputs the detected signal having information on a tissue mode in the subject body to the image processing circuit 18. Whereas, the CFM mode processing unit 17b performs a frequency analysis on rate information from the electric signal received from the transmission and reception circuit 16 and outputs the analysis result to the image processing circuit 18 as a signal having information on a moving speed of the blood flow or tissue in the subject body.

The image processing circuit 18 receives the signals from the B mode processing unit 17a and the CFM mode processing unit 17b. Based on the control of the system controller 15, the image processing circuit 18 structures various images related to a B mode image and a CFM image be overlapped or arranged, and also performs a variety of quantitative analysis and measurement based on these images to conduct an image processing on adding information representing the result on the images. Then, the image processing circuit 18 converts the image signal into a scan signal for a TV to be output to the monitor 14. With this configuration, as illustrated in FIG. 1, the ultrasonic images (including various images related to the B mode image and the CFM image, information related to the measurement and the analysis result, etc.) IM are displayed on monitor 14.

In addition, the image processing circuit 18 has a function as display image generating means according to the present invention. During the operation of the WFS 2 or the movement (transfer) thereof, based on the control of the system controller 15, in addition to the operation panel 13, in response to the instruction from the operation device 3, the image processing circuit 18 converts the various image signals such as a menu, an icon, and a character string for the WFS 2 and the transfer into the scan signal for the TV to be output to the monitor 14. With this configuration, as illustrated in FIG. 2, in addition to the ultrasonic image IM, as a display screen for the WFS 2, for example, a WFS menu screen M1, which will be described later, including an image of the icon or the character string is displayed on the monitor 14 at an appropriate position. The WFS menu screen is displayed on the monitor 14 at the time of the execution of a program of the WFS 2 by the system controller 15. Furthermore, the image processing circuit 18 also has a function of displaying, when the user registration information (user information) such as the WFS 2 or the diagnosed examination data is moved (transferred) among the plurality of ultrasonic imaging diagnostic apparatuses 1A to 1N, the transfer source or the transfer destination on the monitor 14.

The system controller 15 has a function as control means of the present invention, a driver apparatus for a CPU (processor), a memory (RAM/ROM), a hard disk device, a removal medium (such as a CD-ROM, a floppy (registered trademark) disk, and a memory card) connected to an internal bus, for example, which is not illustrated in the drawing, and a function as a computer having other peripheral apparatuses. The operation of the entire ultrasonic imaging diagnostic apparatus 1 is controlled in accordance with the procedure previously programmed at the time of the examination. This control operation is performed on the operation panel 13 as well as in response to the instruction from the operation device 3 and based on the respective modes of the diagnosis, the examination, the display, etc., the transmission and reception conditions, and the like.

The WFS 2 is structured by software executed through the operation of the system controller 15 and, for example, the work flow system disclosed in Japanese Unexamined Patent Application Publication No. 2001-137237 is applied to the WFS 2. On the basis of data on an operation order (hereinafter also referred to as "work flow data") in which an execution order (hereinafter also referred to as "work flow program") of a plurality of execution items (hereinafter also referred to as "activities") executed through the operations of the apparatus main body 11 is previously determined, the system (WFS) 2 is configured to subsequently read out and execute sub programs corresponding to a plurality of activities (hereinafter also referred to as "activity program") for switching the operations of the apparatus main body 11 and also to be capable of change the execution order of the activities in accordance with the operation of the operation device 3.

The WFS 2 includes, as an example of the software module configuration, as illustrated in FIG. 1, a work flow data storage unit 21 for storing the work flow data, an activity program storage unit 22 for storing the activity program, and a work flow engine unit 23 for reading out the activity program corresponding to each of the activities in the respective stages of the work flow from the activity program storage unit 22 based on the work flow data of the work flow data storage unit 21 for execution.

The operation device 3 is configured to be able to perform a remote operation by way of a communication with the apparatus main body 11, and may employ a wired or wireless communication mode. In either case, a device accommodating space and a scheme for the communication are required, but according to this example, both the wired and wireless communication modes are applied.

It should be noted that according to the wired communication mode, a code hanging arm for avoiding a contact of the code to a floor or a cord accommodation function such as a cord reel function is required. In contrast, the wireless communication mode is superior to the wired communication mode in the aspects of movement the operability due to the following reasons: 1) when moving around with the operation device 3, the cord is not caught in a surrounding device, a drip stand, or the like, 2) a wire does not contact the patient and the patient does not feel unpleasant sensation, 3) there is no contact of the code to the floor or the like as no code is provided and this is preferable from the aspect of hygiene, etc.

For the operation device 3, any types may be applied as long as the device has a size and shape appropriate for the operator to be able to operate the on hands at a location away from the apparatus main body 11 such as a bed side of the subject, for example, a small-sized handy type which the operator can easily grip by hand (palm size), a frat placement console type (for example, at a size equal to or smaller than A4) which can be placed on the bed side of an examination room, or a stationary type. The type is selected in accordance with a preference of the doctor, the technician, or the like. In addition, the operation device 3 may be structured to be detachably attached to the apparatus main body 11.

As an example illustrated in FIG. 2, the operation device 3 accommodates a power source unit 31a such as a battery inside a device main body 31 and the respective units operated by way of the power supply from power source unit 31a, that is, a host controller 32 in charge of the control center such as a CPU and various controllers and interfaces connected to the host controller 32 including various switch controllers 33, a microphone controller 34, a speaker controller 35, a vibration mechanism controller (driver circuit such as a motor) 36, a display unit controller 37, a wireless communication interface (infrared communication (IrDA), electric waves (based on a predetermined wireless communication standard such as Bluetooth or IEEE802.11) or the like) 38, a communication interface (based on a predetermined communication standard such as USB or IEEE1394) 39, and a transfer memory 40 for incorporating the user information transfer program.

It should be noted that the user information includes a work flow protocol (work flow data), screening data (diagnosis result) of a patient (subject), a key arrangement of a panel of the respective ultrasonic imaging diagnostic apparatuses 1A to 1N, a position and a height of the panel, a monitor luminance, an image quality condition, a setting of body marks, settings of various measurement methods, default setting values thereof, personal information related to the user and the subject themselves, etc. Also, the user information is information recorded (saved) in the work flow data storage unit 21 functioning as the recording means by the users such as the doctors of the ultrasonic imaging diagnostic apparatuses 1A to 1N.

Also, the user information transfer program is a program for transferring the above-mentioned user information respectively saved in the work flow data storage unit 21 of a predetermined one of the ultrasonic imaging diagnostic apparatuses 1A to 1N to the work flow data storage unit 21 of a different one of the ultrasonic imaging diagnostic apparatuses 1A to 1N. That is, this user information transfer program is a program for selectively transferring the predetermined information among the above-mentioned user information through the execution by the host controller 32 and causing the antenna unit of the respective ultrasonic imaging diagnostic apparatuses 1A to 1N to wirelessly transmit a control instruction (command) signal for appropriately displaying a necessary display for this transfer on the monitor 14 of the ultrasonic imaging diagnostic apparatuses 1A to 1N for each predetermined step via the wireless communication interface 38.

Furthermore, the user information transfer program is provided with a personal authentication program. Before the user information is transferred, this identical person authentication program is activated to certify whether the operator (user) of the operation device 3 is an identical person who has a permission to be able to use the operation device 3 for accessing and transferring the user information.

In addition, a plurality of allocation changeable switches SW1, SW2, . . . , SWn, a microphone 41 for a voice input such as a finding of the doctor, a speaker 42 for a voice output, a vibration mechanism 43 such as a vibrator, a display unit 44 such as various indicators (LED) or a liquid crystal display, and an antenna unit 45 such as an infrared communication window or a wireless antenna which are connected to the host controller 32 via various controllers 33 to 37 and an interface 38 are mounted to the operation device 3.

The host controller 32 is composed of, for example, an IC (integrated circuit) unit such as a mouse controller to which a CPU is mounted, but the host controller 32 may be structured as a combined IC unit by including at least a part of other controllers 33 to 37 and the interfaces 38 and 39.

The host controller 32 transmits, in accordance with the operation of the operator, control instructions (commands) S1 such as various switch commands which are previously set for the apparatus main body 11 via the wireless communication interface 38 or the communication interface 38, and also receives from the system controller 15 of the apparatus main body 11 via the wireless communication interface 20 or the communication interface 19, various control instructions (commands) S2 such as an alarm which will be described later. The host controller 32 controls the operation of the ultrasonic imaging diagnostic apparatus 1 through the above-mentioned command transmission and reception.

Any type of switch elements such as a push type and an image rotation type (rotary encoder, etc.) can be applied to the plurality of switches SW1 to SWn of the operation device 3. For example, these switch elements are structured of an element having an optical sensor mechanism. In this case, such effects can be attained that the cleaning performance is improved while no concave and convex parts (grooves) and no driver unit are provided to facilitate the maintenance or the switch elements attached with contamination prevention covers are used while taking advantage of the absence of the concave and convex parts.

Various switch elements such as a movement button, an execution button, and a switching button necessary for the operation of the WFS 2, and a user information transfer mode switch are provided to the above-mentioned respective switches SW1 to SWn as an example.

When a WFS menu M1 (or M2) is displayed on the monitor 14 together with the ultrasonic image IM and the WFS 2 is operated, these respective switches SW1 to SWn execute the following functions, for example.

That is, with the switch SW1, based on a control instruction thereof (switch command) S1, in a case where an icon type WFS menu screen is displayed, any one of activity is determined with an icon. In a case where a character string type WFS menu screen is displayed, any one of activity is determined with a character string A2. With this configuration, the corresponding activity program is called and executed on the WFS 2 side and other menus are determined.

The switch SW2 is a user information transfer mode switch and composed of, for example, a push type execution button. When the switch SW2 is turned ON to be operated, the ON operation is read by the host controller 32, and also the user information transfer program is read from the memory 40. Thus, the identical person authentication program in the program is first activated and executed. Next, after it is certified that the operator is the identical person, the host controller 32 activates the user information transfer program main body and transmits the user information transfer control instruction (command) signal from the wireless communication device 45 to the transfer destination of the ultrasonic imaging diagnostic apparatuses 1A to 1N.

Based on control instruction (switch command) S1, for example, in a case where the character string type WFS menu screen is displayed on the monitor 14, in addition to this screen, the switch SW3 activates a highly flexible pop-up screen such as a forcible termination or another scenario calling and displays such a screen at an appropriate position (although not described in this example, the pop-up screen may be activated when the WFS 2 is not operated).

As illustrated in FIG. 1, in the operation device 3, the switches SW1 to SW4 are arranged on a frat top face of the portable device main body 31, and the switches SW5 and SW6 are provided to a side face of the device main body 31.

The switch SW1 is composed of a push type execution button for determining an item such as an activity during the WFS operation, a direction key for moving in the up, down, left, and right directions for selecting an item such as an activity, and a direction key (track ball function) with which a two dimensional position can be specified such as a cursor movement as well as a gain control switch which utilizes the rotary encoder mechanism.

The switch SW2 is composed of a push type execution button and functions as a user registration information transfer mode selection switch. The switch SW3 is composed of an execution button for activating the pop-up menu.

Furthermore, the switch SW4 on the right-hand side at the device front center is composed of a freezing execution button for stopping (freezing) the display screen irrespective of the time of the WFS operation and the normal examination.

In addition, the switch SW5 is composed of a push type execution button for the print (print out) which is not particularly set in the above-mentioned example. Furthermore, the switch SW6 is composed of a rotary type button with which a view depth of an ultrasonic image obtained through the ultrasonic scan can be adjusted.

Then, as the WFS scenario may differ for each operator in the WFS 2, the operation device 3 is provided with at least one function of voice recognition, finger print recognition, and retina recognition, for example, as the authentication for certifying whether the operator is the identical person. As the user such as the doctor or the technician is known through this identical person authentication, it is possible to easily call the WFS scenario in a folder managed by the user itself. Also, it is desirable that the operation device 3 is provided with a function of specifying a device ID. This is because interference is prevented from occurring when a plurality of operation devices are used at the same time.

It should be noted that the meaning of the normal examination switch (key) and the above-mentioned switch is, for example, that it is possible to freely allocate the key which is frequently utilized in the ultrasonic imaging diagnostic apparatus 1 by the user (which can be functioned as a custom button).

In addition to the above, the respective switches SW1 to SWn also include, for example, a recording instruction switch dedicated to the microphone 41 and the like.

When the above-mentioned respective switches SW1 to SWn are operated, under the control of the various switch controller 33 and the host controller 32, the control instructions s1 for switch commands (arbitrary commands can be prescribed) in accordance with the types of the movement button, the execution button, the switching button, and the like which are allocated to the operated switches SW1 to SWn are transmitted via the wireless communication interface 38 or the communication interface 38 from the operation device 3 side to the apparatus main body 11 side.

As a result, on the apparatus main body 11 side, in accordance with the control instruction s1 of the operation device 3 side, the change in the operation of the WFS 2 and the transfer of the WFS 2 can be performed by the system controller 15.

For example, the system controller 15 reads out and executes the activity program with respect to the activity selected with the image of icon or the character string of the activity on the monitor 14 when the control instruction s1 through the operation of the movement button during the execution of the WFS 2 or selected through the operation of the movement button when the control instructions s1 is received upon the operation of the execution button.

At the same time, the image processing unit 18 performs a change such as a color change or lighting so that the image display state of the icon or the character string of the activity selected through the operation of the movement button can be visually grasped on the monitor 14.

The microphone 41 is adapted to input a voice input at least including a finding of the doctor or the like so that the voice input can be recorded. In a case where the above-described dedicated recording switch is provided on the operation device 3, the voice input from the microphone 41 is recorded while this recording switch is pressed. At this time, the switch is lighted as illumination on the display unit 44 (such as an LED) so that the user can understand that the recording is being performed. Also, the recording stop is executed when the recording switch is released, and when the recording is not executed, the switch is turned OFF.

In addition, the voice signal input from the microphone 41 is automatically recorded in report data as voice data or character data obtained through a character conversion after the voice recognition by using known voice recognition and character conversion function which is not illustrated in the drawing.

Furthermore, the voice signal input from the microphone 41 can also be utilized as a command for controlling the operation of the ultrasonic imaging diagnostic apparatus 1 through the voice recognition. For example, in the WFS 2, at the time of the execution of the WFS 2, the examination progress is automatically performed only by selecting the image of the icon or the character string or the like for the activity from the WFS menu on the monitor 14. Therefore, the control can be performed with a relatively small number of simple commands such as "Next" for advancing the WFS menu, "Return (Back)" for the selection in a reverse way, and "OK" for prompting the determination, and a problem of a voice recognition rate is practically cleared. Thus, the control with high reliability can be performed.

The speaker 42 works in collaboration with the alarm function, for example, on the apparatus main body 11 side. In accordance with the control instruction s2 from the apparatus main body 11 side, for example, when an alarm informing that the patient has an electrocardiographic abnormality or the like, that effect can be announced by a voice, or when a mode in the contrast echocardiography is switched, that effect can also be announced by a voice.

The vibration mechanism 43 works, similarly to the above-mentioned speaker 42, for example, in collaboration with the alarm function on the apparatus main body 11 side and receives the control instruction s2 from the apparatus main body 11 side. For example, when an alarm informing that the patient has an electrocardiographic abnormality or the like is required, or when a mode in the contrast echocardiography is switched, the vibration can be performed in order to inform the operator of the operation device 3 of that effect.

Such an alarm is issued to the doctor or the technician who is the operator by way of the sound from the speaker 42 or the vibration from the vibration mechanism 43 through the operation device 3. The alarm function at this time is particularly useful when another examination action is desired to be taken by the doctor or the technician based on the examination plan, for example, when it is considered that the examination in another mode is desired to be taken, when a time elapsing a certain period of time is desired to be found out in consideration of the throughput, or when there is an electrocardiographic abnormality or the like in the vitality of the patient.

For example, in the contrast echocardiography, a time management is required based on the respective phases (for example, in the case of an abdominal area, there are kindred terms depending on a time after the contrast agent injection including an arterial phase, an arterial/portal phase, a perfusion phase, and the like). In a usual case, a timer displayed on the screen of the monitor 14 is referred to. However, in order to maintain the scan cross section or concentrate on the screen, it is often difficult to execute the examination while the time is managed. For this reason, adequate human resources for managing the time are secured in advance depending on site.

In contrast, by informing the operator of timer information by ways of an alarm sound, an audio guide, or a vibration every required elapsed time using the operation device 3 working in collaboration with the timer function, for example, it is possible to reduce the number of above-mentioned human resources for managing the time. In addition, as the progress state of the WFS 2 is informed by using the audio guidance, the progress of the WFS 2 can be realized more smoothly. Also, caution information may be informed as well. Examples of the audio guidance at this time are represented as follows. 1) Progress content example: "Contrast agent is injected", "Mode is changed", 2) Time management example: "(After the contrast agent injection) 30 seconds", "(After the contrast agent injection) 4 minutes 30 seconds", 3) Caution item example: "MO is not set".

Then, as illustrated in FIG. 2, the operation device 3 is provided with the transfer memory 40 saving the user information transfer program. This user information transfer program and the host controller 32 for executing this user information program compose user information transfer means. That is, the host controller 32 reads the transfer memory 40 from the user information transfer program for the activation when a state in which the user information transfer mode selection switch SW2 is turned ON and operated is detected. Then, the host controller 32 transmits a control instruction (command) to the antenna unit 20a of the apparatus main body 11 via the wireless communication interface 38 and the antenna unit 45 for transferring the user registration information such as the work flow data of the predetermined WFS 2 mounted to each of the transfer source ultrasonic imaging diagnostic apparatuses 1A to 1N to the work flow data storage unit 21 of the different ultrasonic imaging diagnostic apparatuses 1A to 1N functioning as the transfer destination.

Figure 3:
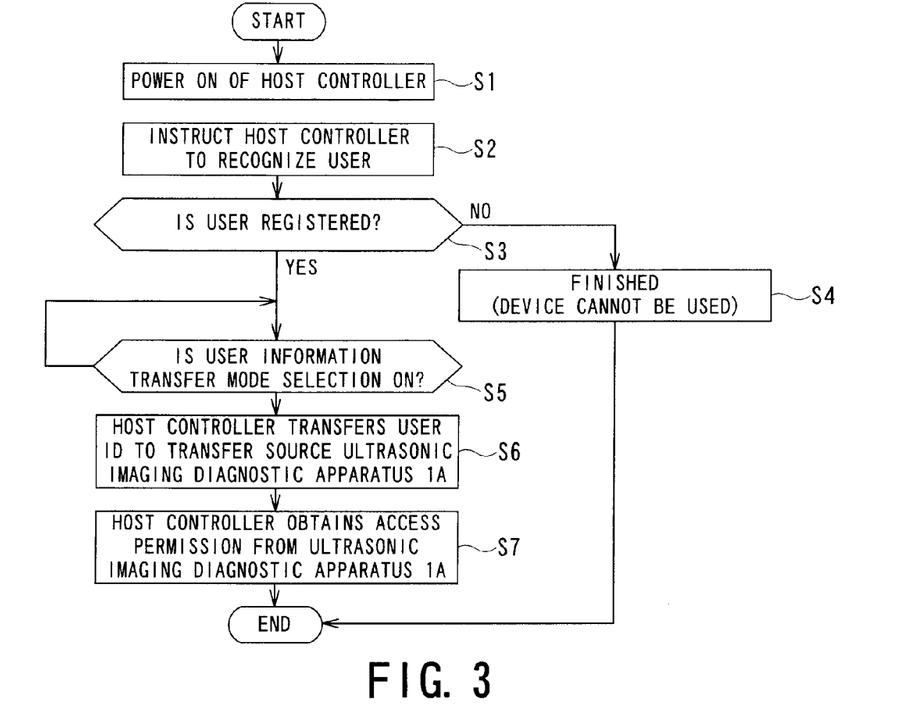
FIG. 3 is a flowchart of an identical person authentication program in a user registration information transfer program according to the embodiment illustrated in FIG. 1.
Figure 4:
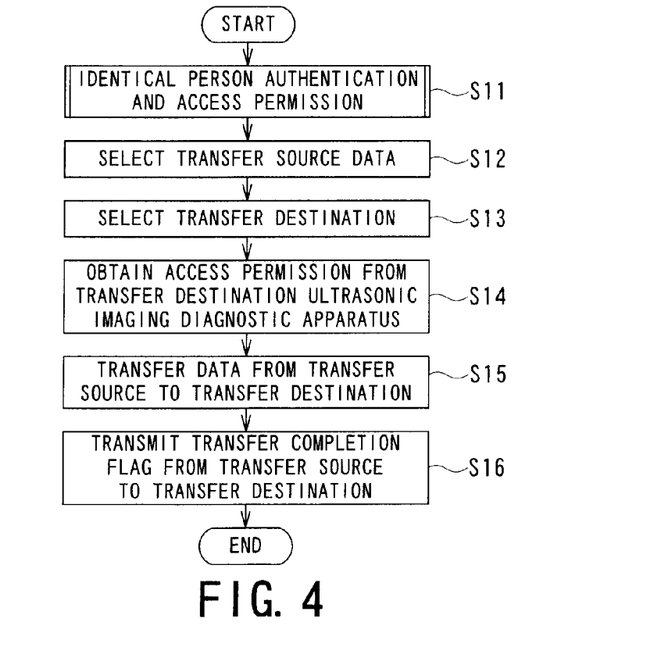
FIG. 4 is a flowchart of a main part of the user registration information transfer program according to the embodiment illustrated in FIG. 1.

FIG. 3 is a flowchart of an identical person authentication program in this user registration information transfer program. FIG. 4 is a flowchart of a program for transferring predetermined user registration information from a predetermined transfer source to a predetermined transfer destination via the LAN 4 after the identical person authentication through the execution of the identical person authentication program. In these flowcharts, reference symbols obtained by adding numerals to the alphabet S represent the respective steps in the flowcharts.

That is, as illustrated in FIG. 3, first, in Step S1, the host controller 32 reads a state whether a power source switch (not illustrated) of the operation device 3 is turned ON and operated. When the state in which the power source switch is turned ON and operated is read, next, a user ID is input or the user is recognized through the user recognition function such as the voice recognition or the finger print recognition of the operation device 3 in Step S2. For example, the user input its own voice to the microphone 41 or puts its own finger print on a fingerprinting sensor plate (not illustrated) to recognize the user.

After that, next, in Step S3, it is determined whether the ID, voice, finger print, or the like of the user, which is recognized through this user recognition function is matched with the previously registered user ID, voice, finger print, or the like, of the user who is permitted itself to access the registration information ID. In this Step S3, in the case of No, in other words, when the user is not registered in advance, in Step S4, for example, this authentication program is ended while an LED lamp or the like indicating, for example, that the access is not permitted, which is not illustrated in the drawing, is turned ON, and the process cannot be advanced to the user information transfer program.

On the other hand, in Step S3, when the user is registered in advance, as the case of Yes, the process is advanced to the next Step S5, where it is repeatedly detected whether the user information transfer mode selection switch SW2 of the operation device 3 is turned ON and operated. When it is detected that the user information transfer mode selection switch SW2 is turned ON and operated, in other words, in the case of Yes, the process is advanced to the next Step S6. In this Step S6, the user ID is transmitted to the predetermined ultrasonic imaging diagnostic apparatus functioning as the transfer source of the user information, for example, the ultrasonic imaging diagnostic apparatus 1A, via the wireless communication interface 38. It should be noted that the user information which the user is not permitted to access is displayed gray down, and the operation of the operation device 3 is prohibited.

The system controller 15 of the transfer source ultrasonic imaging diagnostic apparatus 1A having received this user ID detects whether this received ID is registered in the work flow data storage unit 21 as the ID of the user who is permitted to access the user information. When the system controller 15 detects that the received ID is registered, an access permission signal is returned via the wireless communication interface 20 and the antenna unit 20a to the operation device 3. In Step S7, the host controller 32 of the operation device 3 receives this access permission signal via the antenna unit 45 and the wireless communication interface 38 to confirm that the user is permitted to access the user information. With this configuration, the host controller 32 ends the individual person authentication program, and also the process is shift to the user information transfer program illustrated in FIG. 4.

That is, as illustrated in FIG. 4, in Step S11, when the host controller 32 of the operation device 3 confirms the user authentication and the access permission to the user information of the transfer source ultrasonic imaging diagnostic apparatus 1A, in the next Step S12, transfer data that is transferred this time is selected from among the user information that should be transferred.

To be precise, the user information includes work flow data, a key arrangement and a height of the panel of the respective ultrasonic imaging diagnostic apparatuses 1A to 1N, a monitor luminance, an monitor image quality condition, a setting of body marks, settings of various measurement methods, default setting values thereof, examiner registration data, etc., which are individually set by the user, and which item is selected among from these items to be transferred to the transfer destination ultrasonic imaging diagnostic apparatuses 1A to 1N.

Figure 5:
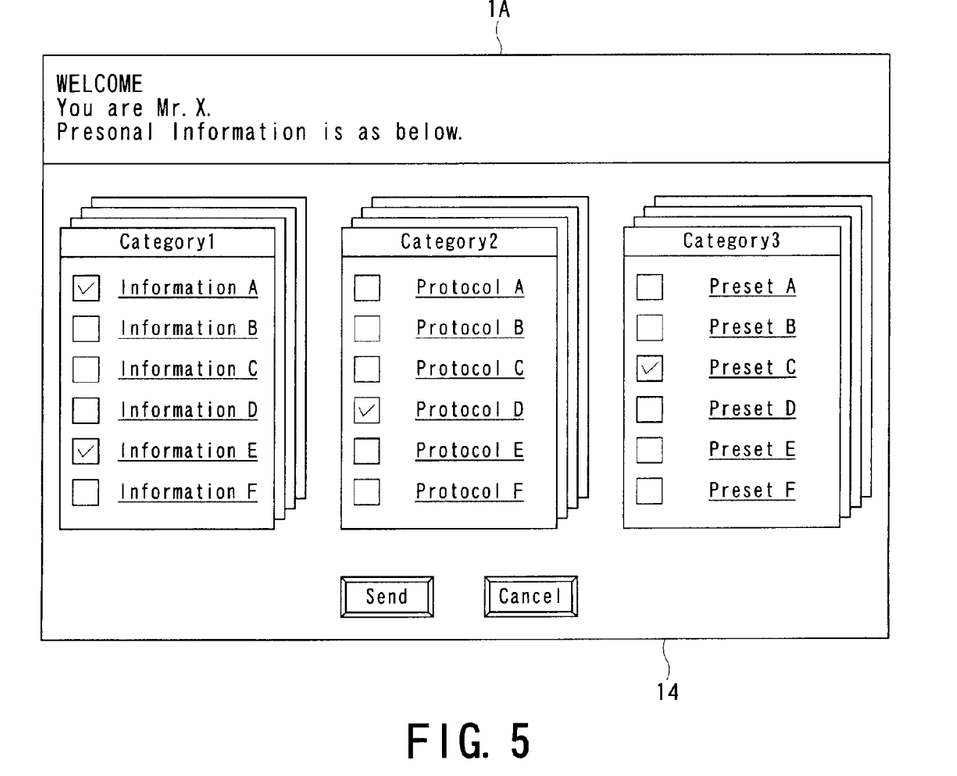
FIG. 5 illustrates a screen example for selecting from among user registration information an item to be transferred, which is displayed on a monitor of a transfer source ultrasonic imaging diagnostic apparatus illustrated in FIG. 1.

FIG. 5 illustrates a display screen example displayed on the monitor 14 of the transfer source ultrasonic imaging diagnostic apparatus 1A, for example, when the item that should be transferred is selected from among items of the user information allocated to Category 1 to 3. In FIG. 5, "information A to E" represents, for example, examiner registration data, "Protocol A to F" represents work flow protocols, "Preset A to E" represents setting values and the like. In addition, "Send" is a display button for selecting the item that should be transferred and "cancel" is a display button for canceling the selection.

In the next Step S13, a transfer destination of the ultrasonic imaging diagnostic apparatuses 1B to 1N of this selected item is selected by the user.

Figure 6:
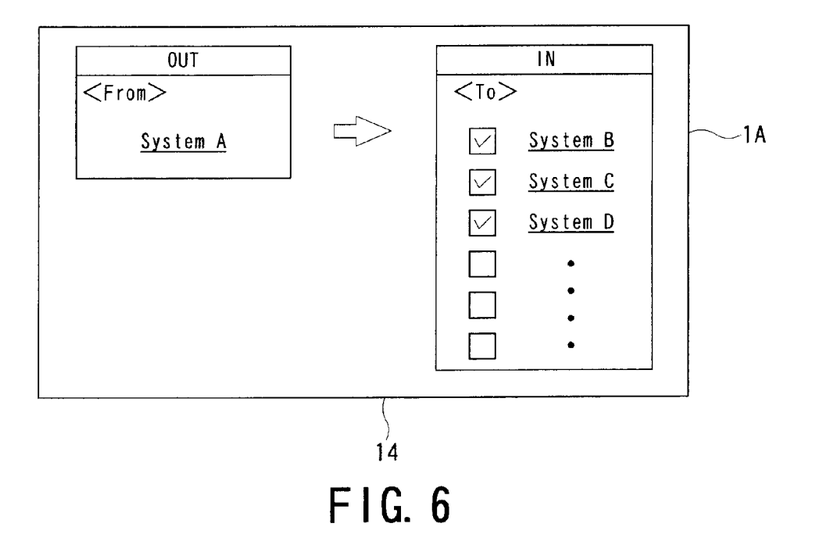
FIG. 6 illustrates a screen example for selecting a transfer destination, which is displayed on the monitor of the transfer source ultrasonic imaging diagnostic apparatus illustrated in FIG. 1.

FIG. 6 illustrates a display screen example displayed on the monitor 14 of the transfer source ultrasonic imaging diagnostic apparatus 1A when this transfer destination of the ultrasonic imaging diagnostic apparatuses 1B to 1N is selected.

In FIG. 6, <From> System A indicates that the transfer source ultrasonic imaging diagnostic apparatus 1A and <To> Systems B, C, . . . , N indicates that the transfer destination ultrasonic imaging diagnostic apparatuses 1B, 1C, . . . , 1N. By checking check boxes, the transfer destination can be selected. This box check is performed with cursor movement means and execution means such as a determination button (not illustrated) of the operation device 3.

Next, in Step S14, the host controller 32 of the operation device 3 transmits the user ID to the selected transfer destination ultrasonic imaging diagnostic apparatuses 1B to 1N, and obtains access permission from these transfer destination ultrasonic imaging diagnostic apparatuses 1B to 1N or at least one of the transfer destination ultrasonic imaging diagnostic apparatuses.

After that, in Step S15, the host controller 32 transmits the selected user information from the transfer source ultrasonic imaging diagnostic apparatus, for example, the ultrasonic imaging diagnostic apparatus 1A to the transfer destination ultrasonic imaging diagnostic apparatuses, for example, the transfer destination ultrasonic imaging diagnostic apparatuses 1B, 1C, . . . , 1N, or at least one of the transfer destination ultrasonic imaging diagnostic apparatuses via the LAN 4.

Figure 7:
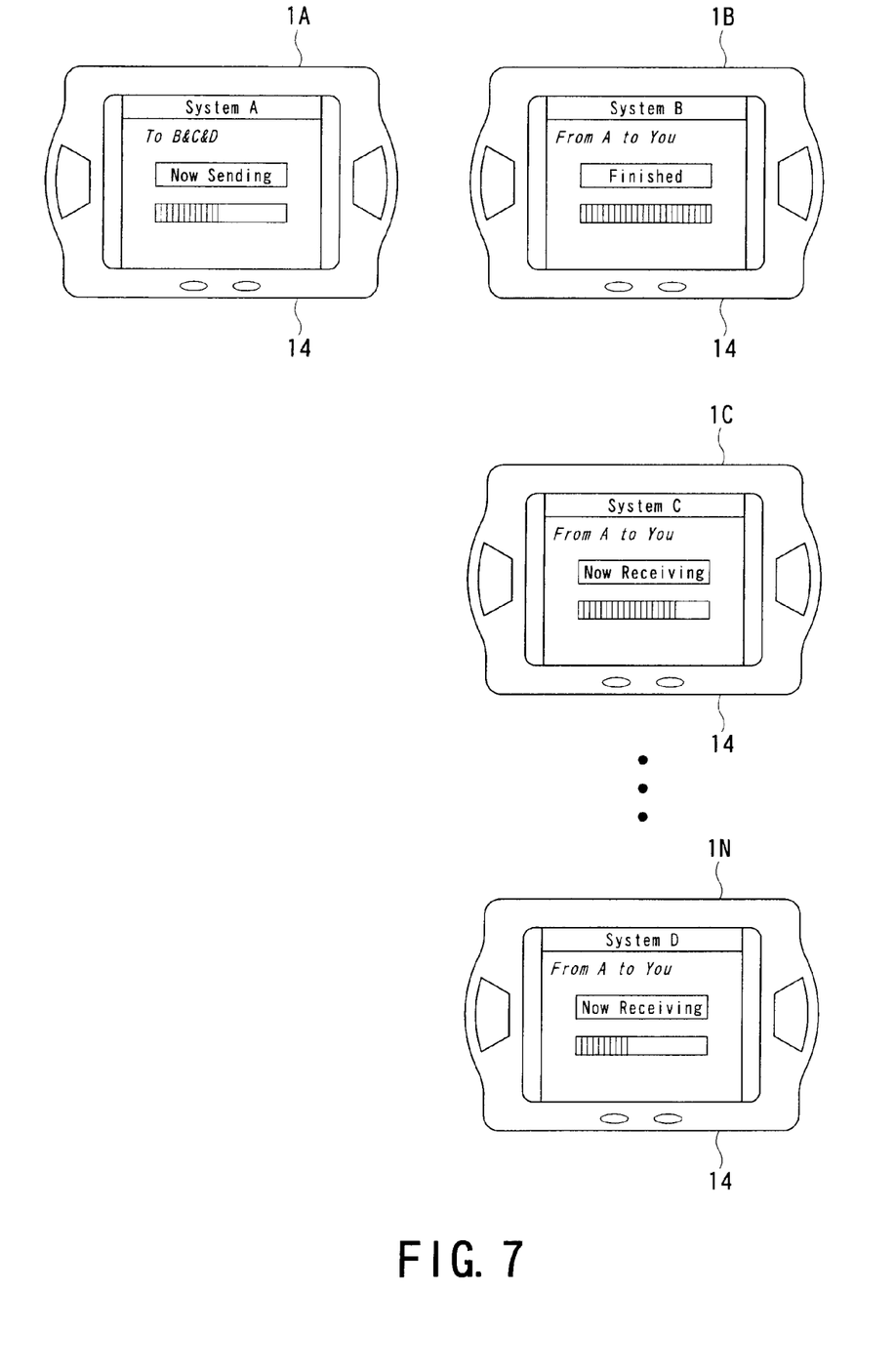
FIG. 7 illustrates examples of displaying the progress or the like of the transfer on the monitor of the respective ultrasonic imaging diagnostic apparatuses when the user registration information is transferred among the plurality of ultrasonic imaging diagnostic apparatuses illustrated in FIG. 1.

FIG. 7 illustrates display examples of the monitor 14 of the respective ultrasonic imaging diagnostic apparatuses 1A to 1N at the time of this user information transfer. The transfer state is displayed by way of, for example, a progress bar or characters ("Finished (transfer competed)", "Now Receiving (receiving)"), and the like. With this configuration, only the particular user information whose access is performed to the user who operates the operation device 3 is transmitted to the permitted transfer destination ultrasonic imaging diagnostic apparatus, for example, the transfer destination ultrasonic imaging diagnostic apparatuses 1B to 1N, or at least one of the transfer destination ultrasonic imaging diagnostic apparatuses.

For this reason, even when the user cannot user the specific accustomed ultrasonic imaging diagnostic apparatus 1A due to any cause, the user information registered to the ultrasonic imaging diagnostic apparatus 1A by the user such as the work flow data of the WFS 2 previously mounted to this ultrasonic imaging diagnostic apparatus 1A, the examiner data, and the setting values can be used also in the transfer destination ultrasonic imaging diagnostic apparatuses 1B to 1N, or at least one of the transfer destination ultrasonic imaging diagnostic apparatuses. Therefore, the transfer destination ultrasonic imaging diagnostic apparatuses 1B to 1N, or at least one of the transfer destination ultrasonic imaging diagnostic apparatuses can be operated like the accustomed ultrasonic imaging diagnostic apparatus 1A. For this reason, it is possible to improve the operation efficiency and the operation accuracy of the ultrasonic imaging diagnostic apparatuses 1B to 1N, or the one of the transfer destination ultrasonic imaging diagnostic apparatuses. With this configuration, the throughput of the routine examination performed by using these ultrasonic imaging diagnostic apparatuses 1B to 1N or at least one of the transfer destination ultrasonic imaging diagnostic apparatuses can be improved.

Also, an access to the user information that can be transferred to different ultrasonic imaging diagnostic apparatuses 1A to 1N or at least one of the ultrasonic imaging diagnostic apparatuses is limited to the user itself whose access is registered in advance and the relevant user information, and thus the security of the user information can be improved.

Furthermore, the operation device 3 and the LAN 4 are used for the transfer and the movement of the user information, and it is therefore to easily, swiftly, and efficiently transfer the user information as compared with a case of transferring the user information by using a removable medium.

Figure 8:
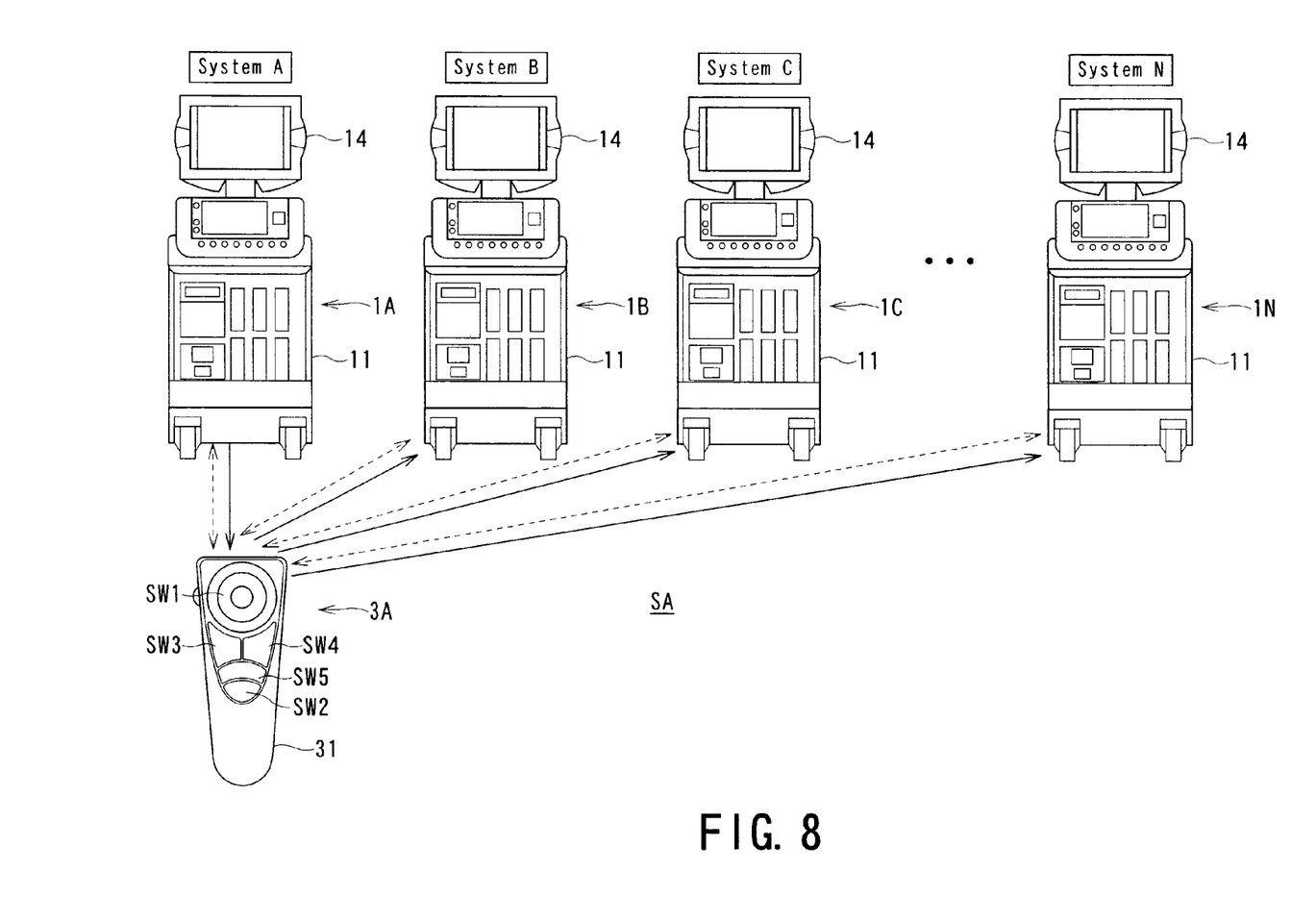
FIG. 8 is a schematic diagram illustrating an entire configuration of a medical diagnostic imaging system according to a second embodiment of the present invention.
Figure 9:
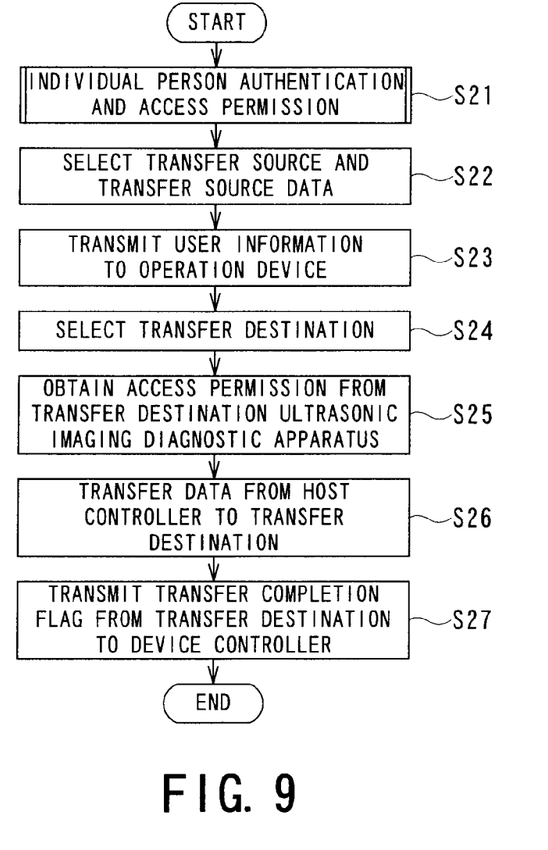
FIG. 9 is a flowchart of a user information transfer program in the medical diagnostic imaging system illustrated in FIG. 8.

FIG. 8 is a schematic diagram illustrating an entire configuration of a medical diagnostic imaging system SA according to a second embodiment of the present invention. FIG. 9 is a flowchart of the same user information transfer program. The medical diagnostic imaging system SA has a feature of transferring the user information such as the WFS 2 mounted to a predetermined ultrasonic imaging diagnostic apparatus, for example, the ultrasonic imaging diagnostic apparatus 1A or the examiner registration data without the LAN 4 using illustrated in FIG. 1, via the user information transfer memory provided to the operation device 3A to different ultrasonic imaging diagnostic apparatuses 1B to 1N or at least one of the ultrasonic imaging diagnostic apparatuses. Other structures are similar to those of the above-mentioned first embodiment.

That is, in the medical diagnostic imaging system SA, the operation device 3 is provided with the user information transfer memory for temporarily saving the user information, and the above-mentioned user information transfer program is replaced by a second user information transfer program. This second user information transfer program is provided with the identical person authentication program for certifying whether the user is registered as the identical person who has the access permit similarly to the above-mentioned user information transfer program. Then, such a configuration is adopted that the user information such as the WFS 2 mounted to the transfer source ultrasonic imaging diagnostic apparatus, for example, the ultrasonic imaging diagnostic apparatus 1A, the examiner registration data, and various setting values of the operation panel is temporarily wirelessly downloaded without the intermediation of the LAN 4 to the user information transfer memory of the operation device 3, and thereafter is again uploaded to the transfer destination ultrasonic imaging diagnostic apparatus, for example, the ultrasonic imaging diagnostic apparatuses B to 1N, or at least one of the ultrasonic imaging diagnostic apparatuses.

In other words, in a case where the power supply switch of the operation device 3 is turned ON and operated and also the user information transfer mode selection switch SW2 is turned ON and operated, when these ON operations are detected by the host controller 32, the host controller 32 first reads out the user information transfer program from the user information transfer memory. Then, as illustrated in FIG. 9, first in Step S21, the identical person authentication program similar to the identical person authentication program illustrated in FIG. 3 is activated. Then, the user inputs necessary data for the identical person authentication, for example by inputting the ID, inputting the predetermined voice to the microphone 41 of the operation device 3, or putting the finger print on the finger print sensor plate. After that, regarding the user information that should be transferred of the transfer destination ultrasonic imaging diagnostic apparatus, for example, the ultrasonic imaging diagnostic apparatus 1A, the host controller 32 of the operation device 3 determines whether the user is the identical person who is permitted to access. When the identical person authentication is denied, a transfer prohibition lamp (LED) or the like (not illustrated) of the operation device 3 is turned ON to end the identical person authentication program and the user information transfer program.

On the other hand, in Step S21, when the identical person authentication indicates that the user is the access permitted person, in the next Step S22, the transfer source ultrasonic imaging diagnostic apparatus, for example, the ultrasonic imaging diagnostic apparatus 1A and items of the user information desired to be transferred to the user information transfer memory of the operation device 3 are selected with the user information selection means in the operation device 3. The selection of the items of the user information that are going to be transferred from now is executed through the operation of the selection means in the operation device 3 while the user looks at the screen displayed on the monitor 14 of the transfer source ultrasonic imaging diagnostic apparatus 1A as illustrated in FIG. 6 similarly to the above-mentioned first embodiment.

Figure 10:
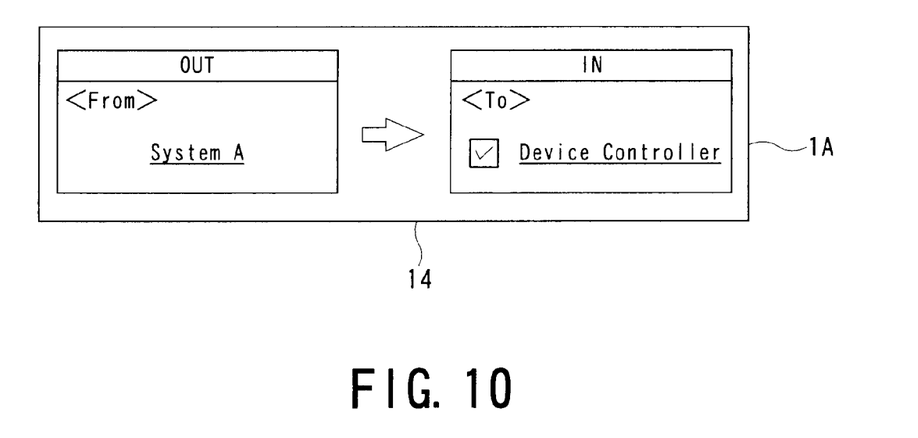
FIG. 10 illustrates an example of displaying a state in which the user registration information is transferred from the transfer destination ultrasonic imaging diagnostic apparatus to operation device on a monitor of a transfer destination center server according to the embodiment illustrated in FIG. 8.

FIG. 10 illustrates a screen example displayed on the monitor 14 of the transfer source ultrasonic imaging diagnostic apparatus 1A. In the drawing, <From> "System A" indicates the transfer source ultrasonic imaging diagnostic apparatus 1A and <To> "Device Controller" indicates the host controller 32 of the operation device 3 which is a point of passage of the user information.

After that, in Step S23, through the ON operation of the user information transfer mode selection switch SW2 of the operation device 3, the selected user information that is also mounted to the transfer source ultrasonic imaging diagnostic apparatus 1A is wirelessly downloaded from the transfer source ultrasonic imaging diagnostic apparatus 1A to the operation device 3, temporarily stored in the user information transfer memory, and saved.

In the next Step S23, the transfer destination ultrasonic imaging diagnostic apparatus, for example, the ultrasonic imaging diagnostic apparatuses 1B to 1N or at least one of the ultrasonic imaging diagnostic apparatuses to which the information is further transferred from the operation device 3 is selected by the user. This transfer destination selection can be performed through a method of inserting checks in the check boxes displayed on the monitor 14 of the transfer source ultrasonic imaging diagnostic apparatus 1A or the like as illustrated in FIG. 6 similarly to the above-mentioned first embodiment.

In the next Step S25, a request signal for requesting the access permission is wirelessly transmitted from the host controller 32 of the operation device 3 to the thus selected transfer destination ultrasonic imaging diagnostic apparatuses 1B to 1N or at least one of the ultrasonic imaging diagnostic apparatuses, and the host controller 32 receives the access permission signal from the transfer destination ultrasonic imaging diagnostic apparatuses 1B to 1N or at least one of the transfer destination ultrasonic imaging diagnostic apparatuses.

In the next Step S26, the host controller 32 reads out the user information whose transfer permission is obtained, from the user information transfer memory and uploads the user information to the ultrasonic imaging diagnostic apparatuses 1B to 1N or at least one of the ultrasonic imaging diagnostic apparatuses having obtained the access permission.

For this reason, the system controller 15 of the ultrasonic imaging diagnostic apparatuses 1B to 1N or at least one of the ultrasonic imaging diagnostic apparatuses stores and saves this transferred user information in the work flow data storage unit 21.

After that, in Step S27, the system controller 15 wirelessly transmits a user information transfer completion flag to the operation device 3 to complete the user information transfer and ends the user information transfer program.

Therefore, according to the medical diagnostic imaging system SA, without using the LAN 4, it is possible to easily and swiftly transfer the user information of the transfer source ultrasonic imaging diagnostic apparatus, for example, the ultrasonic imaging diagnostic apparatus 1A to the transfer destination ultrasonic imaging diagnostic apparatuses 1B to 1N or at least one of the ultrasonic imaging diagnostic apparatuses.

For this reason, the different ultrasonic imaging diagnostic apparatuses 1B to 1N or at least one of the ultrasonic imaging diagnostic apparatuses can be fully used almost as if the user operates the accustomed transfer source ultrasonic imaging diagnostic apparatus 1A. As a result, it is possible to improve the throughput of the routine examination which uses the ultrasonic imaging diagnostic apparatuses 1A to 1N or at least one of the ultrasonic imaging diagnostic apparatuses.

It should be noted that according to the above-mentioned embodiments, the case in which the user information transfer means is provided to the operation device 3 has been described, but the present invention is not limited to the above. For example, this user information transfer means may be provided on the side of the ultrasonic imaging diagnostic apparatuses 1A to 1N.

That is, such a configuration may be adopted that a memory for recording the user information transfer program is provided to the ultrasonic imaging diagnostic apparatuses 1A to 1N, the system controller 15 is provided with a function of executing this user information transfer program as the CPU, a command signal for performing a control such as activation or stopping of this user information transfer program is wirelessly transmitted to the ultrasonic imaging diagnostic apparatuses from the operation device 3, and the transfer of the user information is remotely controlled.

In addition, as described above, the host controller 32 of the operation device 3 has the identical person authentication function. With a resident communication function between the operation device 3 and the apparatus main bodies 11, 11, 11, ... of the ultrasonic imaging diagnostic apparatuses 1A to 1N, the user approaches the apparatus main bodies 11, 11, 11, ... while carrying with the operation device 3. When the operation device 3 enters the communicable area with respect to the apparatus main body 11, 11, 11, ..., in a case where it is determined that the user is the individual person who previously has the access permission due to the relationship of trust between the user and the apparatus main bodies 11, 11, 11, ..., the login to the apparatus main bodies 11, 11, 11, ... may be automatically activated. In addition, even in the case of the individual person who has the access permission, if a different (another) individual who has the access permission has first logged in the apparatus main bodies 11, 11, 11, ..., even when the individual person who has the access permission while carrying with the operation device 3 approaches the apparatus main bodies 11, 11, 11, ... and the operation device 3 enters the communicable area with respect to the apparatus main bodies 11, 11, 11, ..., this login is not allowed, and the individual person who has first logged in may control the entirely of the apparatus main bodies 11, 11, 11, .... These cases correspond to a case where the main power switches of the apparatus main body 11, 11, 11, ... are in a standby state while being turned ON and operated. However, even when the main power switches of the apparatus main bodies 11, 11, 11, ... are not turned ON, the individual person who similarly has the access permission approaches the apparatus main bodies 11, 11, 11, .... When the operation device 3 is within the communicable area with respect to the apparatus main bodies 11, 11, 11, ..., the main power switches of the apparatus main body 11, 11, 11, ... may be automatically turned ON and then the login to the apparatus may be automatically urged.

Furthermore, according to the above-mentioned embodiments, the user information such as the work flow system (the WFS 2) is registered in the memories of the apparatus main bodies 11, 11, 11, ..., in the ultrasonic imaging diagnostic apparatuses 1A to 1N, but this user information may be stored in a memory in the operation device 3. In that case, it is unnecessary to transfer (mode) the user information among the ultrasonic imaging diagnostic apparatuses 1A to 1N. If the operation device 3 alone is provided, whatever the statuses of the apparatus main bodies 11, 11, 11, ... are, the execution of the activity program can be performed in a user's unique manner. Thus, the examination can be efficiently advanced by executing the operation method of the ultrasonic imaging diagnostic apparatuses 1A to 1N in accordance with the user's unique technique and skill.

What is claimed is:
1. A medical diagnostic imaging system comprising:
   a plurality of ultrasonic imaging diagnostic apparatuses; and
   an operation device connected to the ultrasonic imaging diagnostic apparatuses so as to be able to perform a data communication, wherein:
   each ultrasonic imaging diagnostic apparatus comprises:
      a recording unit configured to record user information registered by a user operating the operation device, the user information including work flow data customized for the user for guiding at least an operation procedure of the ultrasonic imaging diagnostic apparatus;
      an execution unit configured to execute the user information recorded by the recording unit;
      a transfer unit configured to transfer to a different one of the plurality of the ultrasonic imaging diagnostic apparatuses the user information recorded by the recording unit; and the operation device comprises:
- a first memory unit configured to memorize authentication information used for authenticating the user operating the operation device;
- an access restriction unit configured to authenticate whether or not the user operating the operation device is permitted to access an ultrasonic imaging diagnostic apparatus of the plurality of the ultrasonic imaging diagnostic apparatuses on the basis of the authentication information memorized in the first memory unit, and if the user operating the operation device is permitted to access the ultrasonic imaging diagnostic apparatus, permitting an access to the ultrasonic imaging diagnostic apparatus, and if the user operating the operation device is not permitted to access the ultrasonic imaging diagnostic apparatus, restricting the access to the ultrasonic imaging diagnostic apparatus; and
- a control unit configured to control operation of the ultrasonic imaging diagnostic apparatus to control a transfer of the user information to the different ultrasonic imaging diagnostic apparatus by the transfer unit;

wherein the recording unit is further configured to record the user information transferred from a transfer unit of the different ultrasonic imaging diagnostic apparatus.

2. The medical diagnostic imaging system according to claim 1, wherein:
the control unit is further configured to control to permit the operation of the ultrasonic imaging diagnostic apparatus if the access to the ultrasonic imaging diagnostic apparatus is permitted by the access restriction unit, and is configured to control to partly restrict the operation of the ultrasonic imaging diagnostic apparatus if the access to the ultrasonic imaging diagnostic apparatus is restricted by the access restriction unit, and
the part of the operation of the ultrasonic imaging diagnostic apparatus controlled to restrict by the control unit includes at least the user information browsing, duplicate of the user information, transfer of the user information by the transfer unit, starting the ultrasonic imaging diagnostic apparatus, and log in to the ultrasonic imaging diagnostic apparatus.

3. The medical diagnostic imaging system according to claim 1, wherein each ultrasonic imaging diagnostic apparatus further comprises a display unit configured to display a transfer state of the user information in a case that the user information is transferred to the different one of the ultrasonic imaging diagnostic apparatuses by the transfer unit.

4. The medical diagnostic imaging system according to claim 1, wherein:
the operation device further comprises:
a download unit configured to download the user information from the ultrasonic imaging diagnostic apparatus if the access to the ultrasonic imaging diagnostic apparatus is permitted by the access restriction unit;
a second memory unit configured to memorize the user information downloaded from the ultrasonic imaging diagnostic apparatus by the download unit;
an upload unit configured to upload to a different one of the plurality of the ultrasonic imaging diagnostic apparatuses the user information memorized in the second memory unit; and
the recording unit is further configured to record the user information updated by the upload unit of the operation device.

5. The medical diagnostic imaging system according to claim 1, wherein the control unit is further configured to control so as to boot the ultrasonic imaging diagnostic apparatus when the access to the ultrasonic imaging diagnostic apparatus is permitted by the access restriction unit.

6. The medical diagnostic imaging system according to claim 1, wherein the control unit is further configured to control so as to permit log into the ultrasonic imaging diagnostic apparatus when the access to the ultrasonic imaging diagnostic apparatus is permitted by the access restriction unit.

7. An information processing method for a medical diagnostic imaging system including a plurality of ultrasonic imaging diagnostic apparatuses and an operation device connected to the ultrasonic imaging diagnostic apparatuses so as to be able to perform a data communication, wherein:
performing by each ultrasonic imaging diagnostic apparatus the following:
recording user information registered by a user operating the operation device, the user information including work flow data customized for the user for guiding at least an operation procedure of the ultrasonic imaging diagnostic apparatus;
executing the user information recorded by the recording unit;
transferring to a different one of the plurality of the ultrasonic imaging diagnostic apparatuses the user information recorded by the recording unit; and
performing by the operation device the following:
memorizing authentication information used for authenticating a user operating the operation device;
authenticating whether or not the user operating the operation device is permitted to access an ultrasonic imaging diagnostic apparatus of the plurality of the ultrasonic imaging diagnostic apparatuses on the basis of the authentication information memorized in the operation device, and if the user operating the operation device is permitted to access the ultrasonic imaging diagnostic apparatus, permitting an access to the ultrasonic imaging diagnostic apparatus, and if the user operating the operation device is not permitted to access the ultrasonic imaging diagnostic apparatus, restricting the access to the ultrasonic imaging diagnostic apparatus; and
controlling operation of the ultrasonic imaging diagnostic apparatus, to control the transferring the user information to the different ultrasonic imaging diagnostic apparatus;
wherein each ultrasonic imaging diagnostic apparatus performs recording the user information transferred from a transfer unit of the different ultrasonic imaging diagnostic apparatus.

8. A medical diagnostic imaging system comprising:
a plurality of ultrasonic imaging diagnostic apparatuses; and
an operation device connected to the ultrasonic imaging diagnostic apparatuses so as to be able to perform a data communication, wherein:
each ultrasonic imaging diagnostic apparatus comprises:
a recording unit configured to record user information registered by a user operating the operation device, the user information including work flow data customized for the user for guiding at least an operation procedure of the ultrasonic imaging diagnostic apparatus;
an execution unit configured to execute the user information recorded by the recording unit;

a transfer unit configured to transfer to a different one of the plurality of the ultrasonic imaging diagnostic apparatuses the user information recorded by the recording unit;

the operation device comprises:
- a first memory unit configured to memorize authentication information used for authenticating the user operating the operation device;
- an access restriction unit configured to authenticate whether or not the user operating the operation device is permitted to access an ultrasonic imaging diagnostic apparatus of the plurality of the ultrasonic imaging diagnostic apparatuses on the basis of the authentication information memorized in the first memory unit, and if the user operating the operation device is permitted to access the ultrasonic imaging diagnostic apparatus, permitting an access to the ultrasonic imaging diagnostic apparatus, and if the user operating the operation device is not permitted to access the ultrasonic imaging diagnostic apparatus, restricting the access to the ultrasonic imaging diagnostic apparatus, and
- a control unit configured to control operation of the ultrasonic imaging diagnostic apparatus, to control a transfer of the user information to the different ultrasonic imaging diagnostic apparatus by the transfer unit;

wherein the recording unit is further configured to record the user information transferred from a transfer unit of the different ultrasonic imaging diagnostic apparatus.

9. An ultrasonic imaging diagnostic apparatus connected to different ultrasonic imaging diagnostic apparatuses and connected to an operating device so as to be able to perform data communication with one another, comprising:
- a recording unit configured to record user information registered by a user operating the operating device, the user information including work flow data customized for the user for guiding at least an operation procedure of the ultrasonic imaging diagnostic apparatus;
- an execution unit configured to execute the user information recorded by the recording unit;
- a transfer unit configured to transfer to the different ultrasonic imaging diagnostic apparatus the user information recorded by the recording unit; and wherein the operating device comprises:
- a control unit configured to control operation of the ultrasonic imaging diagnostic apparatus;
- the control unit is further configured to control a transfer of the user information to the different ultrasonic imaging diagnostic apparatus by the transfer unit;

wherein the recording unit is further configured to record the user information transferred from a transfer unit of the different ultrasonic imaging diagnostic apparatus.

10. An operation device connected to a plurality of ultrasonic imaging diagnostic apparatuses so as to be able to perform data communication with one another, comprising:
- a first memory unit configured to memorize authentication information used for authenticating a user operating the operation device;
- an access restriction unit configured to authenticate whether or not the user operating the operation device is permitted to access an ultrasonic imaging diagnostic apparatus of the plurality of the ultrasonic imaging diagnostic apparatuses on the basis of the authentication information memorized in the first memory unit, and if the user operating the operation device is permitted to access the ultrasonic imaging diagnostic apparatus, permitting an access to the ultrasonic imaging diagnostic apparatus, and if the user operating the operation device is not permitted to access the ultrasonic imaging diagnostic apparatus, restricting the access to the ultrasonic imaging diagnostic apparatus; and
- a control unit configured to control operation of the ultrasonic imaging diagnostic apparatus, to control the ultrasonic imaging diagnostic apparatus to transfer user information to different ones of the plurality of the ultrasonic imaging diagnostic apparatuses wherein each ultrasonic imaging diagnostic apparatus comprises:
- a recording unit configured to record user information registered by a user operating the operation device, the user information including work flow data customized for the user for guiding at least an operation procedure of the ultrasonic imaging diagnostic apparatus;
- an execution unit configured to execute the user information recorded by the recording unit;
- a transfer unit configured to transfer to a different one of the plurality of the ultrasonic imaging diagnostic apparatuses the user information recorded by the recording unit; and the operation device comprises:
- a first memory unit configured to memorize authentication information used for authenticating the user operating the operation device;
- an access restriction unit configured to authenticate whether or not the user operating the operation device is permitted to access an ultrasonic imaging diagnostic apparatus of the plurality of the ultrasonic imaging diagnostic apparatuses on the basis of the authentication information memorized in the first memory unit, and if the user operating the operation device is permitted to access the ultrasonic imaging diagnostic apparatus, permitting an access to the ultrasonic imaging diagnostic apparatus, and if the user operating the operation device is not permitted to access the ultrasonic imaging diagnostic apparatus, restricting the access to the ultrasonic imaging diagnostic apparatus; and
- a control unit configured to control operation of the ultrasonic imaging diagnostic apparatus, to control a transfer of the user information to the different ultrasonic imaging diagnostic apparatus by the transfer unit;

wherein the recording unit is further configured to record the user information transferred from a transfer unit of the different ultrasonic imaging diagnostic apparatus.

11. The medical diagnostic imaging system according to claim 1, wherein:
- the user information further includes a registration data customized for the user, and
- the registration data includes settings of predetermined measurement methods, each settings customized for the user.

12. The medical diagnostic imaging system according to claim 1, wherein the control unit is further configured to control operation of the ultrasonic imaging diagnostic apparatus to permit the transfer of the user information to the different ultrasonic imaging diagnostic apparatus by the transfer unit if the access to the ultrasonic imaging diagnostic apparatus and an access to the different ultrasonic imaging diagnostic apparatus are permitted by the access restriction unit, and is further configured to control operation of the ultrasonic imaging diagnostic apparatus to restrict the transfer of the user information to the different ultrasonic imaging diagnostic apparatus by the transfer unit if at least one of the access to the ultrasonic imaging diagnostic apparatus and the access to the different ultrasonic imaging diagnostic apparatus is restricted by the access restriction unit.

13. The information processing method according to claim 7, wherein the controlling operation of the ultrasonic imaging diagnostic apparatus is controlling operation of the ultrasonic imaging diagnostic apparatus to permit the transferring the user information to the different ultrasonic imaging diagnostic apparatus if the access to the ultrasonic imaging diagnostic apparatus and an access to the different ultrasonic imaging diagnostic apparatus are permitted in the authenticating, and controlling operation of the ultrasonic imaging diagnostic apparatus to restrict the transferring the user information to the different ultrasonic imaging diagnostic apparatus if at least one of the access to the ultrasonic imaging diagnostic apparatus and the access to the different ultrasonic imaging diagnostic apparatus is restricted in the authenticating.

14. The medical diagnostic imaging system according to claim 8, wherein the control unit is further configured to control operation of the ultrasonic imaging diagnostic apparatus to permit the transfer of the user information to the different ultrasonic imaging diagnostic apparatus by the transfer unit if the access to the ultrasonic imaging diagnostic apparatus and an access to the different ultrasonic imaging diagnostic apparatus are permitted by the access restriction unit, and configured to control to restrict the transfer of the user information to the different ultrasonic imaging diagnostic apparatus by the transfer unit if at least one of the access to the ultrasonic imaging diagnostic apparatus and the access to the different ultrasonic imaging diagnostic apparatus is restricted by the access restriction unit.

15. The ultrasonic imaging diagnostic apparatus according to claim 9, wherein the control unit is further configured to control to permit the transfer of the user information to the different ultrasonic imaging diagnostic apparatus by the transfer unit if an access from the operation device to the ultrasonic imaging diagnostic apparatus and an access from the operation device to the different ultrasonic imaging diagnostic apparatus are both permitted as a consequence of authentications performed by the operation device and an operation device of the different ultrasonic imaging diagnostic apparatus respectively, and is further configured to control to restrict the transfer of the user information to the different ultrasonic imaging diagnostic apparatus by the transfer unit if at least one of the access to the ultrasonic imaging diagnostic apparatus and the access to the different ultrasonic imaging diagnostic apparatus from the operation device is restricted as the consequence of the authentications, the authentications performed based on an authentication information for determining whether or not the user operating the operation device is permitted to access the ultrasonic imaging diagnostic apparatus and the different ultrasonic imaging diagnostic apparatus.

16. The operation device according to claim 10, wherein the control unit is further configured to control operation of the ultrasonic imaging diagnostic apparatus to permit the ultrasonic imaging diagnostic apparatus to transfer the user information to the different ultrasonic imaging diagnostic apparatuses if the access to the ultrasonic imaging diagnostic apparatus and an access to the different ultrasonic imaging diagnostic apparatus are permitted by the access restriction unit, and is further configured to control operation of the ultrasonic imaging diagnostic apparatus to restrict the ultrasonic imaging diagnostic apparatus to transfer the user information to the different ultrasonic imaging diagnostic apparatus if at least one of the access to the ultrasonic imaging diagnostic apparatus and the access to the different ultrasonic imaging diagnostic apparatus is restricted by the access restriction unit.

* * * * *